United States Patent [19]

Ranly

[11] Patent Number: 4,859,186

[45] Date of Patent: Aug. 22, 1989

[54] PULPOTOMY AGENT AND METHOD OF USE

[75] Inventor: Don M. Ranly, San Antonio, Tex.

[73] Assignee: Biomedical Development Corporation, San Antonio, Tex.

[21] Appl. No.: 153,137

[22] Filed: Feb. 8, 1988

[51] Int. Cl.$^4$ .............................. A61C 5/00; A61K 6/06
[52] U.S. Cl. .................................. 433/228.1; 106/35; 514/694; 514/698; 514/705
[58] Field of Search ........................ 514/698, 694, 705; 433/228.1; 106/35

[56] References Cited

U.S. PATENT DOCUMENTS

| | | | |
|---|---|---|---|
| 3,912,809 | 10/1975 | Rendon | 424/75 |
| 3,983,252 | 9/1976 | Buchalter | 424/333 |
| 4,048,336 | 9/1977 | Winicov et al. | 514/694 |
| 4,093,744 | 6/1978 | Winicov et al. | 514/705 |
| 4,173,653 | 11/1979 | Law | 514/705 |
| 4,320,157 | 3/1982 | von Hagens | 428/13 |

OTHER PUBLICATIONS

Teplitsky, Paul E. and Rick Grieman, "History of Formocresol Pulpotomy," 8 J. Canada Dent. Assn. 629, (1984).
Ranly, D. M., and Franklin Garcia Godoy, "The Diffusion of Glutaraldehyde from Zinc Oxide-Eugenol Cement," 7 Pediatric Dentistry 215, (Sep. 1985).
Bimstein; Enrique, "Pulpotomy Treatment in Primary Teeth," VI (8) The Compendum of Continuing Education, Articles #4 586, (Sep. 1985).
Ranly, D. M., D. Horn and T. Zislis, "The Effect of Alternatives to Formocresol on Antigenicity of Proteins," 64 J. Dent. Res. 1225-1228, (Oct. 1985).
Garcia-Godoy, Franklin, "A 42 Month Clinical Evaluation of Glutaraldehyde Pulpotimies on Primary Teeth," 10 J. Pododont. 148-155, (Winter 1986).
Ranly, D. M., and Barbara Bayan, "The Effect of Formocresol on Lipids of Bovine Pulp," 12 Journal of Endodontics 559, (1986).
Ranly, D. M., Franklin Garcia Godoy and Diane Horn, "Time, Concentration, and PH Parameters for the Use of Glutaraldehyde as a Pulpotomy Agent: An In Vitro Study," 9 Pediatric Dentistry 199, (Sep. 1987).
Ranly, DDS, PhD., Don M., "Glutaraldehyde Purity and Stability: Implications for Preparation, Storage, and Use as a Pulpotomy Agent", 6 Pediatric Dentistry 83 (Jun. 1984).
Ranly, DDS, PhD., Don M., "Formocresol Toxicity, Current Knowledge", 5 Acta Odontol. Pediat. 93-98 (Dec. 1984).
Ranly, D. M., "A Comparative Study of the Effects of Formaldehyde, Glutaraldehyde and Dimethylsuberimidate on Enzyme Activity in the Bovine Dental Pulp", 5 Acta Odontal. Pediat. 5-8, (6/84).
Ranly, DDS, PhD., Don M., "Pulp Therapy in Primary Teeth, A Review and Prospectus," 3(2) Acta Odontol. Pediat. 63-68, (Dec. 1982).
Ranly, DDS, PhD., Don M., "The Effect of PH and Concentration on the Glutaraldehyde Fixation of Bovine Pulp, An in Vitro Study", 4 Acta Odontol. Pediat. 45-47, (Dec. 1983).
Ranly, D. M. and E. P. Lazzari, "A Biochemical Study of Two BiFunctional Reagents as Alternative to Formocresol," 62 J. Dent. Res. 1054-1057, (Oct. 1983).
S-Gravenmade E. J., "Some Biochemical Consider- (List continued on next page.)

Primary Examiner—Prince E. Willis
Assistant Examiner—Linda D. Skaling
Attorney, Agent, or Firm—Cox & Smith

[57] ABSTRACT

Composition for use as a pulpotomy agent having glutaraldehyde as the active ingredient in a solution stabilized by a buffer suitable for maintaining the pH of the glutaraldehyde solution at near-physiological levels. The stable composition also includes the anti-oxidants sodium nitrite and glycerol. The composition is used by direct application to infected coronal pulp tissue to fix the tissues and prevent further deterioration caused by pulpitis. A method of treating the infected tissue prior to dental restoration is also disclosed.

2 Claims, 2 Drawing Sheets

OTHER PUBLICATIONS ations of Fixation in Endodontics", Journal of Endodontics 7 (Jul. 1975).

Kopel, D.D.S., M. S., Hugh M., Saul Bernick PhD., Estaurdo Zachrisson, CD., Sarabella A. DeRomero, CD., "The Effects of Glutaraldehyde on Primary Pulp Tissue Following Coronal Amputation: An In Vivo Historological Study", 47 Journal of Dentistry for Children 425 (1980).

Lewis, DDS, Bradley Ben, Stanley B. Chestner, DDS, "Formaldehyde in Dentistry: A Review of Mutagenic and Carcinogenic Potential", 103 JADA 429 (1981).

Stonehill, A. A., S. Krop, and P. M. Borick, "Buffered Glutaraldehyde—A New Chemical Sterilizing-Solution", (1963).

PULPOTOMY AGENT AND METHOD OF USE

BACKGROUND OF THE INVENTION present invention relates to a stable, glutaraldehyde-containing pulpotomy agent and a method of using that pulpotomy agent for treating the radicular tissue of pulpotomized teeth. More particularly, the present invention relates to a composition for the treatment of affected or infected teeth prior to dental restoration involving a method of application of a glutaraldehyde-containing, stable fixative which has a long shelf life.

Pulpitis, either microbial or traumatic, is often irreversible and requires the removal of the affected or infected coronal pulp tissue. At present, the major treatment modality for cariously involved pulps of primary teeth consists of the fixation of the radicular tissue with formocresol following amputation of the coronal pulp. Formocresol, a formulation of formaldehyde and cresol in a glycerol vehicle, was introduced into dentistry in 1904 ostensibly for the purpose of neutralizing the toxins present in a necrotic pulp. The widespread use of formocresol in pediatric dentistry can be ascribed to Sweet (Sweet, C. A., "Procedure for treatment of exposed and pulpless deciduous teeth," 16 J.A.D.A. 1153 (1930)). The treatment modality he proposed entailed the sealing of a formocresol-moistened cotton pellet into the pulp chamber on three to five occasions to achieve complete fixation. That multiple-visit regime has given way to the popular five minute application which is the standard treatment even today (Doyle, et al., "Formocresol v. calcium hydroxide in pulpotomy", 29 J. Dent. Child. 86 (1962); Emmerson C. C., et al., "Pulpal changes following formocresol applications on rat molars and human primary teeth," 27 S. Calif. State Dent. Assoc. 309 (1959)). The intent of formocresol pulp therapy is to fix and kill the radicular tissue, and the ability of that therapy to accomplish that goal has been repeatedly verified and the therapy has achieved wide popularity. However, that therapy results in no healing whatsoever (Rolling, I. and H. Lambjerg-Hansen, "Pulp condition of successfully formocresol-treated primary molars," 86 Scand. J. Dent. Res. 267 (1978)), and recent evidence has demonstrated the systemic distribution of topically applied formocresol (Pashley, E. L., et al., "Systemic distribution of $^{14}$C-formaldehyde from formocresol-treated pulpotomy sites," 59 J. Dent. Res. 603 (1980)). There is also an increasing concern regarding the environmental effects of formaldehyde (Report of the Federal Panel on Formaldehyde, R. A. Griesemer, Chairman, 43 Environ. Health Prespect. 139 (1982)), raising concerns about the continued use of this pulpotomy agent.

Other agents have been investigated for use as a pulpotomy agent, including calcium hydroxide and glutaraldehyde. The latter appears to be the recommended alternative (Davis M. J., et al., "Glutaraldehyde: An alternative to formocresol for vital pulp therapy," 49 J. Dent. Child. 176 (1982); s'Gravenmade, E. J., "Some biochemical considerations of fixation in endodontics," 1 J. Endod. 233 (1975)). Glutaraldehyde is known to be an excellent fixative, serving as the standard fixative for electron microscopy, and as an effective disinfectant (Stonehill, A. A., et al., "Buffered glutaraldehyde: A new chemical sterilizing solution," 20 Am. J. Hosp. Pharm. 458 (1963)).

In spite of the proven ability of glutaraldehyde to function as a neutral fixative, there are disadvantages and limitations which have prevented the widespread use of glutaraldehyde as a pulpotomy agent. The most serious of these limitations is a result of the chemical properties of glutaraldehyde. In aqueous solution, glutaraldehyde is mildly acidic, relatively inert, and very stable. Elevation of the pH of an aqueous glutaraldehyde solution increases the microbicidal action of the glutaraldehyde (Stonehill, et al., supra). Unfortunately, at high pH, glutaraldehyde polymerizes, thereby losing that microbicidal activity. A buffer can be used to maintain the pH of the solution at a mildly alkaline level, i.e., at near physiological pH, and sodium phosphate buffer has been used for that purpose, (Ranly, D. M. and E. P. Lazzari, "A biochemical study of two bifunctional reagents as alternatives to formocresol," 62 J. Dent. Res. 1054 (1983)). A sodium bicarbonate buffer can also be used for that purpose, however the results are less satisfactory because that buffer reacts too easily with the protons that are available in the solution to form carbon dioxide, decreasing buffering capability. However, even in a buffered, mildly alkaline solution, glutaraldehyde loses microbial activity eventually as a result of increased polymerization over time, thereby limiting the shelf life of the solution. Such solutions are also sensitive to temperature; exposure to heat increases polymerization such that aqueous glutaraldehyde solutions are routinely stored at cold temperature even for short periods of time.

One alternative that can be utilized to overcome that instability is to prepare a fresh glutaraldehyde solution, buffered to the proper pH, immediately before use of the reagent as a fixative for each pulpotomy procedure. However, a solution which can be used directly without the need for further mixing or additional constituents is far preferable for convenience and has the further advantage of eliminating the potential for addition of improper proportions or incorrect constituents at the time of use. It is, therefore, an object of the present invention to provide a glutaraldehyde-containing pulpotomy agent which retains a high level of fixative activity for long periods of time, thereby insuring that it is immediately and conveniently, available for the effective fixation of tissues and the treatment of infected pulp tissue.

Another object of the present invention is to provide a glutaraldehyde-containing pulpotomy agent which embodies the requisite degree of safety, efficacy, and stability to be capable of fixing a superficial zone of radicular tissue without additional local or systemic effects and which can be stored for long periods of time.

It is another object of the present invention to provide a pulpotomy agent which is compatible with the dental materials which are usually used to restore pulpotomized teeth to form and function.

It is another object of the present invention to provide a composition for use as a pulpotomy agent comprising an aqueous solution of glutaraldehyde, an antioxidant, and a buffer capable of maintaining an alkaline pH.

Another object of the present invention is to provide a pulpotomy agent which is a strong fixative that can cross-link toxins, autolytic enzymes, and necroti pulp, can suppress cell activity to minimize internal resorption, is non-diffusible, exhibits low immunogenicity, is non-mutagenic, and is non-carcinogenic.

SUMMARY OF THE INVENTION

These objects are accomplished by providing a composition for use as a pulpotomy agent comprising between about 2 and about 5% glutaraldehyde, a buffer for maintaining the solution at near physiological pH, and an anti-oxidant. The preferred anti-oxidants are sodium nitrite and/or glycerol.

The present invention is also directed to a method of using that composition for treatment of infected teeth prior to dental restoration comprising mixing the composition with eugenol, adding sufficient zinc oxide to achieve a cement of proper clinical consistency, and applying the cement to the affected pulpal tissue

DETAILED DESCRIPTION OF THE INVENTION

Figure 1:
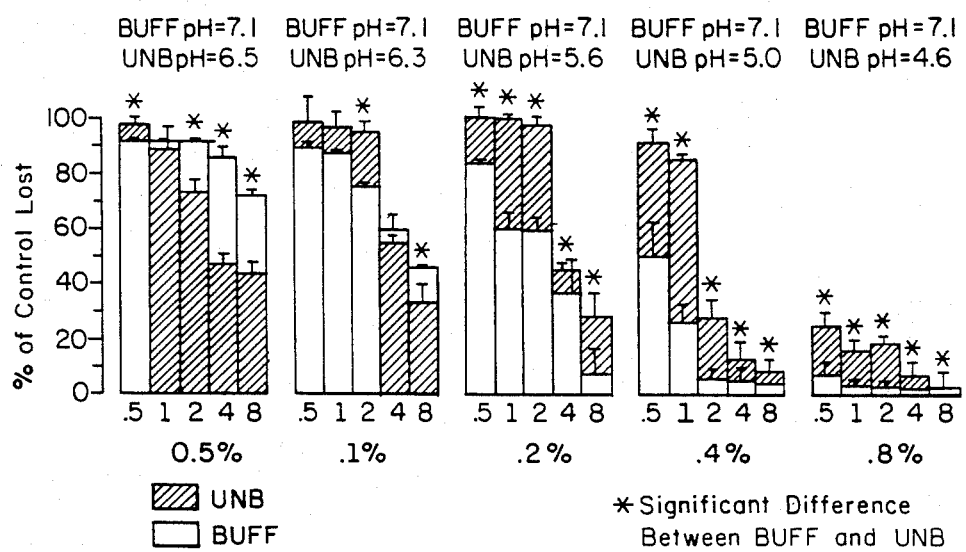
FIG. 1 is a bar graph showing the effect of pH, time, and concentration on the degree of fixation of a 4% glutaraldehyde-containing aqueous solution.

In the following detailed description of the invention, specific examples are given demonstrating the preparation of a presently preferred composition in accordance with the teachings of the present invention (Example I), the efficacy of the composition of the present invention as a fixative (Examples II and III), as well as the stability of that composition (Examples VIII–XI). Two assays were used to evaluate the effectiveness of the composition of the present invention as a pulpotomy agent. The first was based on the diffusion of bovine serum albumin (BSA) from collagen-BSA gel wafers following fixation. That methodology was based on the method described in Flitney, F. W., "The time course of the fixation of albumin by formaldehyde, glutaraldehyde, acrolein and other higher aldehydes," 85 J. Royal Microscop. Soc. 353 (1966)). The collagen-BSA gel was formulated by Flitney to simulate the cytoplasm of the cell. Diffusion of BSA from the gel was intended to provide a reproducible model by which the relative change in the rate of leakage of protein through the cell membrane could be monitored during fixation with different techniques. This procedure was also modified as described in Example III to allow the evaluation of the depth of penetration of the composition of the present invention into adjoining cells of the pulpal tissue. The second assay was the determination of residual lactate dehydrogenase activity (LDH) in bovine pulp following treatment with the composition of the present invention. That assay was based upon the previous demonstration that, the enzyme LDH is a sensitive indicator of biological fixation (Mejare, et al., "Effect of formaldehyde-containing drugs on a human dental pulp evaluated by an enzyme histochemical technique," 84 Scand. J. Dent. Res. 29 (1976)) such that a highly effective fixative would have the effect of eliminating almost all the activity of this enzyme.

Studies were also conducted to determine the optimum concentration, time and pH at which a glutaraldehyde-containing fixative should be applied for effective use as a pulpotomy agent (Examples V–VII). For instance, in Example V, the effect of each of those parameters on the effectiveness of the solution as a fixative was assessed using the collagen-BSA assay of Example II.

The data resulting from the study described in Example V indicate that a neutral environment enhances fixation by dilute preparations of glutaraldehyde. The pH of buffered glutaraldehyde in aqueous solution is normally in the 3.0–4.0 range, presumably as a result of the oxidation of aldehyde moieties to carboxyls. Some of the unbuffered glutaraldehyde solutions used in Example V were so dilute that they did not undergo significant acidic changes; consequently, they exhibited equal or, in some cases, even better fixation than their buffered counterparts. However, when the unbuffered solutions reached decidedly acidic ranges, their ability to cross-link protein was diminished significantly compared to buffered preparations.

The results of the assays described in Examples II–V demonstrated that the extent or quality of fixation (based on the restriction of BSA diffusion from the gels) was directly related to either increasing the concentration of glutaraldehyde or increasing the length of application of any given preparation. For clinical efficiency, the application of higher concentrations of glutaraldehyde for shorter periods of time is preferable to the use of more dilute solutions for longer time intervals. Because a localized, limited zone of fixation of pulp tissue in the vital pulpotomy is an ideal treatment objective, the effect of time and concentration on the depth of penetration was investigated in Example VI. In this assay (described in Example III), the depth of penetration correlates inversely to the efflux of BSA; the deeper the ingress of glutaraldehyde, the less non-cross-linked protein is free for diffusion.

Penetration of glutaraldehyde into the gels was clearly a function of the concentration of glutaraldehyde in he aqueous solution; increased exposure at any given concentration did not enhance the depth of fixation significantly. The results also suggested that glutaraldehyde penetration is self-limiting, tending to reach a common maximum despite ever-increasing concentrations. This conclusion is based on the finding that the secondary diffusion of BSA was decreased by approximately the same amount by the 2, 4, and 8 percent solutions.

The above-described studies revealed characteristics of protein fixation in a restricted environment, and the LDH assay described in Example IV was selected to test the response of pulp tissue to several concentrations and treatments as described in Example VII. The results indicate that LDH inhibition exhibits characteristics of a log-dose response when evaluated at different concentrations for any treatment. However, because exposure time and glutaraldehyde concentration are additive, the degree of fixation can be increased by combining stronger concentrations with longer applications. These findings suggest that the most efficient protocol to enhance fixation should incorporate stronger concentrations of glutaraldehyde.

Another basis for the use of an increased concentration of glutaraldehyde is the maintenance of the number of active molecules in the pulpotomy agent. Even though a 2% solution of buffered glutaraldehyde is a capable histological fixative and disinfectant, as noted above, neutralizing or alkalinating the preparation encourages polymerization. Some of the polymers of glutaraldehyde are formed by reversible aldol condensations (Robertson & Schultz, "The Impurities in Commercial Glutaraldehyde and their Effect on the Fixation of Brain." 30 J. Ultrastructure Res. 275 (1970)), and an equilibrium between monomeric and polymeric forms is reached. While these polymeric forms are still active, the absolute number of cross-linking molecules in the solution is reduced. Should there be any deterioration of the aldehyde moieties, such as oxidation to carboxyls, the adequacy of the 2% preparation is jeopardized. Thus, a slightly higher initial concentration, on the order of the presently preferred 4% concentration, overcomes this unavoidable characteristic of aqueous glutaraldehyde solutions, thereby insuring the maintenance of an adequate number of active molecules. Increasing the concentration in this manner has the additional benefit of insuring adequate fixation even in the face of poor clinical technique and unavoidable polymerization.

The composition of the present invention also includes an anti-oxidant and in a presently preferred embodiment of the invention, the anti-oxidant is a mixture of two anti-oxidants, sodium nitrite and a trihydric alcohol such as glycerol. Sodium nitrite in aqueous solution has a near neutral pH, a property which helps reduce the acidity of glutaraldehyde. Further, in spite of concerns regarding carcinogenic properties, sodium nitrite has been shown to allow a wide margin of safety for use as an anti-oxidant, for instance, in the composition of the present invention.

Glycerol, in addition to functioning as an anti-oxidant, increases the miscibility of the composition of the present invention with zinc oxide-eugenol (ZOE) paste, making possible the incorporation of the fixative into the ZOE sub-base which is customarily applied as a dressing over treated pulp stumps. One drop of eugenol is added to one drop of the composition of the present invention and that mixture is mixed with sufficient zinc oxide to achieve a cement of a proper clinical consistency. That dressing is then placed on the treated canals prior to dental restoration.

The present invention can be better understood by reference to the following examples of specific embodiments of compositions prepared according to the teachings of the present invention.

EXAMPLE I

Preparation of Pulpotomy Agent

A 4% glutaraldehyde pulpotomy agent was prepared by diluting 16 ml E.M. glutaraldehyde (25%, Polyscience Chemical Co.) with 20 ml 9..5% glycerol and 1 mg Sodium Nitrate crystal. The solution is brought up to a volume of 100 mls with sodium phosphate buffer for a total volume of 100 mls. The sodium phosphate buffer was prepared as follows. 27.8 g $NaPO_4$ monobasic crystals in a volumetric flask were brought up to 1000 mls with C.I. $H_2O$. 53.7 g $NaPO_4$ dibasic crystals in a volumetric flask were likewise brought up to 1000 mls. 360 mls of the dibasic solution was then mixed with 140 mls of the monobasic solution to make 500 mls of $NaPO_4$ buffer.

Using this method, solutions have been prepared containing as little as about 2% glutaraldehyde and as much as about 5% glutaraldehyde. Solutions of different concentration can be prepared, of course, by varying the amount of 25% glutaraldehyde to which the other constituents are added. For instance, a 2% solution was prepared by adding those constituents to 8 ml 25% glutaraldehyde and a 5% solution prepared by adding those constituents to 20 ml 25% glutaraldehyde.

EXAMPLE II

Effectiveness of Fixation By Pulpotomy Agents

The effectiveness of the fixative ability of the pulpotomy agent of the present invention was assayed according to the method set out in Flitney, supra. Briefly, that method is as follows. Collagen gels (0.3 g/2.8 ml) were prepared containing a physiological salt solution and bovine serum albumin (1 g BSA/10 ml). The mixture was dissolved in a boiling water bath and measured amounts were pipetted into plastic vials. Collagen-BSA wafers were removed from the vials and incubated in a buffered glutaraldehyde solution and the 4% glutaraldehyde-containing pulpotomy agent prepared as described in Example I, above, for 4 minutes. Wafers treated with distilled water or sodium phosphate buffer for identical time periods were used as respective controls. Following incubation, relative fixation of protein in the gels was ascertained by measuring the amount of BSA which diffuses from the gels into 4 ml of water during a 30 minute period. BSA was quantified by the method described by Bradford, M. M., "A rapid and sensitive method for quantification of microgram quantities of protein utilizing the principles of protein dye binding," 72 Anal. Biochem. 248 (1976).

The quantity of BSA which diffused from each gel is reported below as a percentage of control lost or retained. Each number was calculated from five samples in each group, and the differences between the groups were statistically significant, p 0.001, by Student's t-test.

TABLE 1

|  | Pulpotomy Agent | 4% Glutaraldehyde |
| --- | --- | --- |
| % of control retained | 87 | 78 |

EXAMPLE III

Penetration Of Pulpotomy Agent

The collagen-BSA assay described in Example II, above, was modified to permit the evaluation of the penetration of the pulpotomy agent prepared as described in Example I as follows. Gels were prepared in the same manner as described in Example II, but instead of removing the wafers from the vials and incubating in the various solutions, entire vials with gels intact were submerged in 4% buffered glutaraldehyde and the 4% glutaraldehyde-containing pulpotomy agent of Example I for 4 minutes. Following submersion, the gels were then removed from the vials, placed in distilled water, and the BSA lost assayed as described above. Again, results are expressed as a percentage of control lost or retained as described in Example II and statistics were likewise calculated in the same manner. Differences were not statistically significant.

TABLE 2

|  | Pulpotomy Agent | 4% Glutaraldehyde |
| --- | --- | --- |
| % of control retained | 23 | 27 |

EXAMPLE IV

Determination Of LDH Activity

The effectiveness of the pulpotomy agent prepared as described in Example I, above, was also evaluated by an assay for residual LDH Activity. In this assay, calf pulp was harvested from freshly extracted molars, minced into pieces of approximately 1 mm$^3$, divided into aliquots weighing approximately 0.5 g, and stored at $-20°$ C. until used. After thawing each aliquot was wet weighed and incubated in the 4% glutaraldehyde-containing pulpotomy agent prepared as described in Example I for 4 minutes. The treated sample was homogenized for one minute in ten ml of 0.2M Tris, pH 7.3, using a homogenizer. Following centrifugation for ten minutes at 300 rpm on a clinical centrifuge, the supernatant was decanted. One hundred microliters of the supernatant was added to a cuvette containing 2.8 ml Tris HCl, 1.0 ml of 6.6 mM NaOH, and 0.1 ml of 30 mM sodium pyruvate and vortexed for 10 seconds. The change in absorbence per minute was recorded on a spectrophotometer at 345 nm at room temperature. The activities were calculated as units/g wet weight/min, and the mean was calculated for five samples in each group. The values are reported as a percentage of controls and statistics were the same as described in Example II, above. The differences were not statistically significant.

TABLE 3

|  | Pulpotomy Agent | 4% Glutaraldehyde |
| --- | --- | --- |
| % of control retained | 8.6 | 3.0 |

EXAMPLE V

Effect of pH, Time and Concentration on Degree of Fixation

To determine the effect of pH, time and concentration on the degree of fixation of a glutaraldehyde-containing aqueous solution, collagen-BSA wafers prepared as described in Example II, above, were incubated in buffered and non-buffered solutions of 0 5, 0.1, 0.2, 0.4, or 0.8% glutaraldehyde for 0.5, 1, 2, 4, or 8 minutes. Test solutions were prepared from 25% EM-grade glutaraldehyde; phosphate buffered solutions were adjusted to pH 7.1. Wafers treated with distilled water or buffer for identical time periods were used as respective controls. The quantity of BSA which diffused out of the gels was determined and the results are shown in FIG. 1. The mean and standard deviation were calculated for five samples in each group. Statistical differences between the groups were determined by Student's t-test.

EXAMPLE VI

Effect of Time and Concentration on Depth of Fixation

Figure 2:
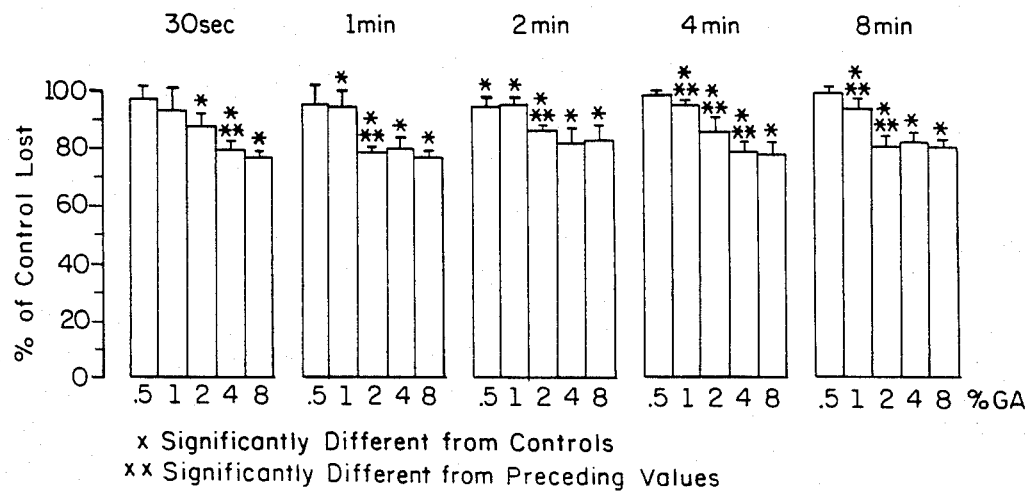
FIG. 2 is a bar graph showing the effect of concentration and length of application of a 4% glutaraldehyde aqueous solution on the depth of fixation using collagen-BSA gels.

To determine the effect of time and concentration on the depth of penetration of a buffered, glutaraldehyde-containing aqueous solution into collagen-BSA gels, vials containing the gel were immersed in 0.5, 1.0, 2.0, 4.0 and 8% glutaraldehyde solutions for 0.5, 1, 2, 4 or 8 minutes as described in Example III, above. Preparation of solutions, handling of controls, sample size, and statistics were the same as described in Example V, and the results are shown in FIG. 2.

EXAMPLE VII

Effect of Concentration and Time on LDH Activity

Figure 3:
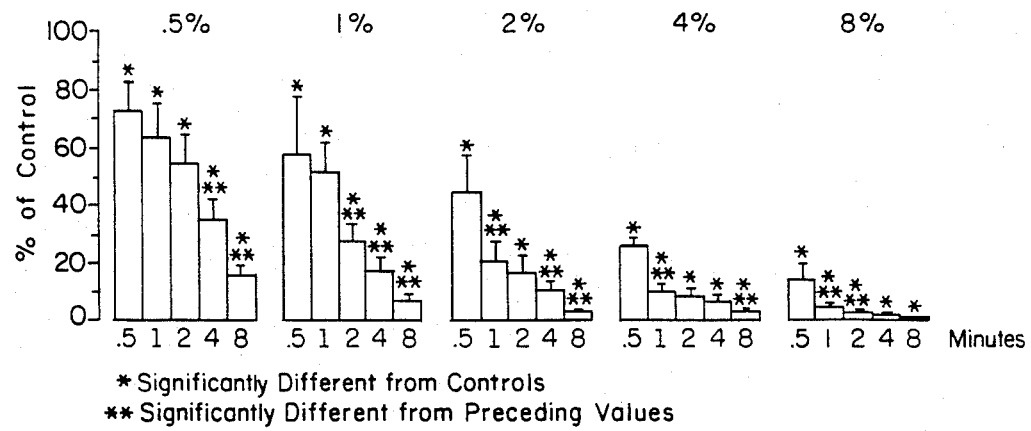
FIG. 3 is a bar graph showing the effect of concentration and length of application of a 4% glutaraldehyde aqueous solution on LDH activity of bovine pulp.

The method described in Example IV, above, was used to assess the effect of different glutaraldehyde concentrations and incubation times on residual LDH activity of bovine pulp. Aliquots of minced calf pulp were incubated in solutions of different glutaraldehyde concentrations prepared as described in Example V for intervals of 0.5, 1, 2, 4, or 8 minutes. The data shown in FIG. 3 are the mean and standard deviation for five samples in each group and are reported as a percentage of controls.

EXAMPLE VIII

Stability Study: Gel Assay

As noted above, the instability of glutaraldehyde solutions is a major disadvantage to the widespread use of glutaraldehyde as a pulpotomy agent. The stability of the pulpotomy agent prepared as described in Example I was, therefore, assayed using the collagen-BSA gel assay described in Example II, above. A control was also run using a 4% buffered glutaraldehyde solution prepared as described in Example V. The percent of control retained is reported in Table 4, below, for a freshly prepared 4% glutaraldehyde solution and the freshly prepared pulpotomy agent described in Example I, a 4% glutaraldehyde solution and the pulpotomy agent described in Example I stored at room temperature (25° C.) for eight months, and for a 4% glutaraldehyde solution and the pulpotomy agent prepared as described in Example I stored at 5° C. for eight months. The assay was repeated with the same solutions diluted ten fold and stored at room temperature or in the cold for nine months rather than eight months. In the case of the full strength data reported in Table 4, the data represents the mean of six samples and for the diluted preparations, the data represents the mean of four samples.

TABLE 4

|  | Glutaraldehyde Solution | | | Pulpotomy Agent | | |
| --- | --- | --- | --- | --- | --- | --- |
|  | Fresh | Room Temp. | Cold | Fresh | Room Temp. | Cold |
| % of control retained (undiluted solutions) | 85 | 85 | 85 | 94 | 94 | 93 |
| % of control retained (diluted 10 fold) | 80 | 72 | 72 | 85 | 67 | 78 |
| % change relative to freshly prepared 4% |  | −11 | −8 | +6 | −17 | −3 |

TABLE 4-continued

| | Glutaraldehyde Solution | | | Pulpotomy Agent | | |
|---|---|---|---|---|---|---|
| | Fresh | Room Temp. | Cold | Fresh | Room Temp. | Cold |
| glutaraldehyde | | | | | | |

EXAMPLE IX

Stability of Pulpotomy Agent: Assay for LDH Activity

The stability of the pulpotomy agent prepared as described in Example I, above, was also assayed by the LDH assay described in Example IV. The data is presented in Table 5 and represent a comparison between a fresh 4% glutaraldehyde solution and the pulpotomy agent freshly prepared as described in Example I, a 4% glutaraldehyde solution and the pulpotomy agent prepared as described in Example I stored at room temperature (25° C.) for eight months, and a 4% glutaraldehyde solution and the pulpotomy agent prepared as described in Example I stored in the cold (5° C.) for eight months. Results reported below are the mean of 5 samples.

TABLE 5

| | Glutaraldehyde Solution | | | Pulpotomy Agent | | |
|---|---|---|---|---|---|---|
| | Fresh | Room Temp. | Cold | Fresh | Room Temp. | Cold |
| % of control retained | 6 | 3 | 4 | 6 | 10 | 11 |

EXAMPLE X

Stability of Pulpotomy Agent: Heat Assays

The stability of the pulpotomy agent of the present invention was also assayed under conditions of heat exposure using the collagen-BSA gel assay described in Example II, above. Activity was compared to the activity of a 4% glutaraldehyde solution which was subjected to the same treatment, i.e., fresh preparation as compared to storage at 37° C. for three months. The data expressed in Table 6 below represent the mean of four samples.

TABLE 6

| | Glutaraldehyde Solution | | Pulpotomy Agent | |
|---|---|---|---|---|
| | Fresh | Heated | Fresh | Heated |
| % of control gel retained | 80 | 53 | 85 | 48 |

EXAMPLE XI

Comparison of Effects of Constituents of Pulpotomy Agent

As described herein, it is the combination of the glutaraldehyde, anti-oxidants and buffering agent which imparts to the pulpotomy agent of the present invention the stability which is so advantageous to the effective use of a glutaraldehyde-containing fixative in dental therapies. The critical nature of the composition of the present invention was assessed by comparing the effects of temperature and long term storage on the pulpotomy agent prepared as described in Example I, above, a 4% glutaraldehyde solution, a 4% glutaraldehyde containing 20% glycerol, and 4% glutaraldehyde containing 1% sodium nitrite. Solutions were either made up fresh, stored for three months at 25° C., or heated to 37° C. for three months as described in Examples IX and X, above and diluted 10 fold for the assay. The collagen-BSA gel assay described in Example II was used to assess the differential effect of the various constituents on stability, and all data represent the mean of four samples.

TABLE 7

| | Fresh Glutaraldehyde | Glutaraldehyde | Pulpotomy Agent | Glutaraldehyde/ Glycerol | Glutaraldehyde/ NaNO2 |
|---|---|---|---|---|---|
| | | Stored at 25° C. for 3 Months | | | |
| % of control retained | 80 | 63 | 70 | 67 | 64 |
| % change relative to fresh glutaraldehyde | | −21 | −13 | −16 | −20 |
| | | Heated at 37° C. for 3 Months | | | |
| % of control retained | 80 | 53 | 48 | 52 | 19 |
| % change relative to fresh glutaraldehyde | | −34 | −41 | −35 | −76 |

The above examples are provided by way of exemplification, and are not intended to operate as a limitation on the scope of the present invention. Changes can be made in the composition of the present invention without departing from the spirit and scope thereof. For instance, those skilled in the art who have the benefit of this disclosure will recognize that when the phrase "4% glutaraldehyde" is used, the percentage of glutaraldehyde in the composition is about 4%. As noted in Example I, the pulpotomy agent of the present invention can be and has been prepared containing from about 2 to about 5% glutaraldehyde and successful clinical therapies have been achieved with glutaraldehyde-containing solutions of those concentrations. Further, the relative proportions of the anti-oxidants sodium nitrite and glycerol are non-critical in the sense that as long as sufficient sodium nitrite and glycerol is present to insure prevention of oxidation of the glutaraldehyde in the composition of the present invention, the stability of the pulpotomy agent will be maintained. Likewise, the proportion of sodium phosphate buffer can be varied so long as sufficient buffer is present to maintain the pH at near-physiological levels. In the case of both the anti-oxidants and the buffering agent, the proportions can be increased in great excess while still insuring the stability of the pulpotomy agent of the present invention. Such changes in the relative proportions of the constituents of the pulpotomy agent of the present invention are specifically contemplated as falling within the scope of the following claims.

What is claimed is:

1. A method of treating infected teeth prior to dental restoration comprising:
    mixing a solution (A) including between 2 and 5% glutaraldehyde, the anti-oxidants sodium nitrite and glycerol in sufficient quantities to maintain the fixative properties of the glutaraldehyde by preventing the oxidation thereof, and a buffer for maintaining the pH of the solution at near-physiological levels, with a solution (B) which consists of eugenol, wherein the proportions of solutions (A) and (B) are approximately equal;
    adding sufficient zinc oxide to achieve a cement of proper clinical consistency; and
2. The method as set forth in claim 1 wherein the buffer is sodium phosphate.

* * * * *